United States Patent [19]

Pfeiffer et al.

[11] 4,239,747
[45] Dec. 16, 1980

[54] DICARBOXYLIC ACID BIS(3,5-DICARBAMOYL-2,4,6-TRIIODOANI-LIDES) USEFUL AS X-RAY CONTRAST AGENTS

[75] Inventors: Heinrich Pfeiffer; Ulrich Speck, both of Berlin, Fed. Rep. of Germany

[73] Assignee: Schering Aktiengesellschaft, Berlin and Bergkamen, Fed. Rep. of Germany

[21] Appl. No.: 2,901

[22] Filed: Jan. 12, 1979

Related U.S. Application Data

[63] Continuation of Ser. No. 806,384, Jun. 14, 1977, abandoned.

[30] Foreign Application Priority Data

Jun. 23, 1976 [DE] Fed. Rep. of Germany ....... 2628517

[51] Int. Cl.³ .................... C07C 103/78; A61K 29/02; C07C 63/24
[52] U.S. Cl. .................... 424/5; 260/544 N; 564/153
[58] Field of Search ...................... 260/544 M, 559 A; 424/5

[56] References Cited

U.S. PATENT DOCUMENTS

| | | | |
|---|---|---|---|
| 2,853,424 | 9/1958 | Priewe et al. | 260/559 R X |
| 3,178,473 | 4/1965 | Hottermann et al. | 424/5 X |
| 3,290,366 | 12/1966 | Hoey | 424/5 X |
| 3,409,662 | 11/1968 | Larsen | 424/5 X |
| 3,557,197 | 1/1971 | Felder et al. | 424/5 X |
| 3,660,464 | 5/1972 | Bernstein et al. | 424/5 X |
| 3,701,771 | 10/1972 | Almen et al. | 260/556 A X |
| 3,732,293 | 5/1973 | Ackerman | 424/5 X |
| 3,939,204 | 2/1976 | Buttermann | 424/5 X |
| 4,001,298 | 1/1977 | Gries et al. | 260/544 M X |
| 4,132,731 | 1/1979 | Klieger et al. | 424/5 |
| 4,139,605 | 2/1979 | Felder et al. | 425/5 |

Primary Examiner—Thomas A. Waltz
Attorney, Agent, or Firm—Millen & White

[57] ABSTRACT

Dicarboxylic acid bis(3,5-dicarbamoyl-2,4,6-triiodoanilides) of the formula

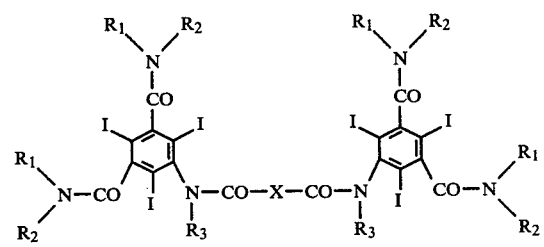

wherein
$R_1$ is lower straight-chain or branched-chain mono- or polyhydroxyalkyl;
$R_2$ is hydrogen, lower alkyl or $R_1$;
$R_3$ is hydrogen or lower alkyl; and
X is a direct bond or straight-chain or branched-chain alkylene interrupted by one or more oxygen or substituted by hydroxy or lower alkyl, are useful in x-ray contrast media.

20 Claims, No Drawings

DICARBOXYLIC ACID BIS(3,5-DICARBAMOYL-2,4,6-TRIIODOANILIDES) USEFUL AS X-RAY CONTRAST AGENTS

This is a continuation of application Ser. No. 806,384, filed June 14, 1977, now abandoned.

BACKGROUND OF THE INVENTION

This invention relates to novel iodoaromatic compounds and their preparation and to x-ray contrast media based thereon.

For examination by roentgenography, for example, of urine-excreting organs and vessels by angiography, compatible salts of 2,4,6-triiodobenzoic acids have been developed as contrast media. These compounds, however, are not tolerated at high dosages without side effects to the human or animal patient, although toxicity is frequently minor. Adequate visualization of the vascular system, the urinary tract, and the cerebrospinal cavities and other systems requires use of high dosages of contrast media, or of highly concentrated solutions. The physico-chemical properties of the contrast media and solutions thereof become important owing to pharmacological effects, including pain, blood pressure drop, and vessel damage attributed to the contrast media.

Dimeric hexaiodated dicarboxylic acids have better neural compatibility and lead to less vasodilation in angiography than monomeric triiodated benzoic acids. Owing to somewhat lower osmotic pressure, for example, dimeric iocarminic acid dimeglumine salt has a relatively high resulting concentration in the urine.

The U.S. Pat. No. 3,701,771 discloses nonionic x-ray contrast media containing, for example, metrizamide, 2-(3-acetamido-5-N-methylacetamido-2,4,6-triiodobenzamido)-2-deoxy-D-glucose. These media are inferior to those of the invention, as will be demonstrated with reference to the tables below.

3-Acylamino-5-alkylcarbamoyl-2,4,6-triiodobenzoic acids are known from U.S. Pat. No. 3,145,197. Several amino acid derivatives of 3-acylamino-5-alkylcarbamoyl-2,4,6-triiodobenzoic acids have likewise been described, e.g., 5-acetamido-2,4,6-triiodoisophthaloyl diglycine in U.S. Pat. No. 3,102,880 and N-[3-N-(alkylacylamino)-5-alkylcarbamoyl-2,4,6-triiodobenzoyl]-amino acids in Helv. Chim. Acta 54 (8): 2551-2559 (1971). Although these compounds have a low toxicity, they have several undesirable side effects. For example, they do not meet the high requirements to be fulfilled by a medium for myelography, e.g., see Ugeskrift for laeger 134 (18): 936 (1972) and Advances in X-Ray Technology 115: 683-684 (1971).

Other teachings on highly iodinated aromatic compounds are those of Erich Klieger et al., U.S. Pat. No. 3,953,501; Heinz Gries et al., U.S. Pat. No. 4,001,298; Heinz Gries, U.S. Pat. No. 3,883,578; and Erich Klieger et al., Ser. No. 555,043, filed Mar. 3, 1975, now U.S. Pat. No. 4,032,567, the disclosures of which are herein incorporated by reference.

SUMMARY OF THE INVENTION

In a compositional aspect, this invention relates to novel compounds of Formula I

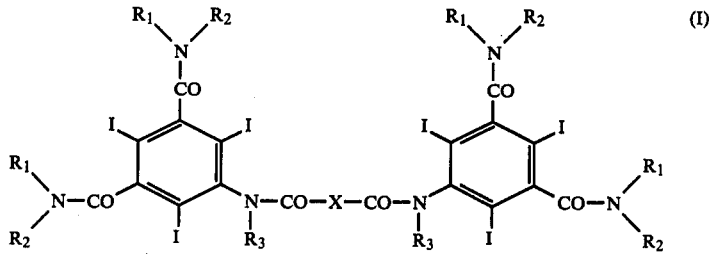

wherein
$R_1$ is alkyl of 2-8 carbon atoms substituted by 1-5 hydroxyl on separate carbon atoms thereof, other than the α-carbon atom,
$R_2$ is hydrogen, alkyl of up to 4 carbon atoms or $R_1$;
$R_3$ is hydrogen or alkyl of 1-4 carbon atoms;
X is a direct bond or straight-chain or branched-chain alkylene, oxaalkylene, dioxaalkylene, or trioxaalkylene of up to 6 carbon atoms, wherein the oxygen atoms of the di- and trioxalkylenes are separated from each other and from the ends thereof by at least one methylene.

This invention relates, in another compositional aspect, to novel tetracarboxylic acid tetrachlorides of Formula II

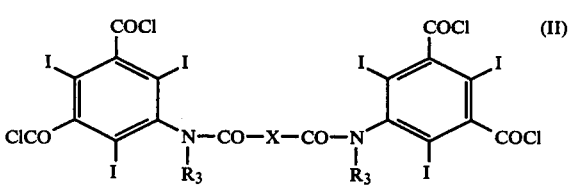

wherein $R_3$ and X are as above, which are intermediates for the preparation of pharmacologically superior novel dicarboxylic acid bis(3,5-dicarbamoyl-2,4,6-triiodoanilides) of Formula I.

In another compositional aspect, this invention relates to an x-ray contrast agent adapted for oral or intravenous administration, comprising a radioopaque amount per unit dosage of a compound of Formula I, in admixture with a pharmaceutically acceptable carrier.

In a method of use aspect, this invention relates to a method for conducting a radiological examination of a patient which comprises administering thereto prior to examination a radioopaque amount of a compound of Formula I.

DETAILED DESCRIPTION $R_1$ is a straight-chain or branched-chain lower mono- or polyhydroxyalkyl of 2-8 carbon atoms, preferably 2-5 carbon atoms. Straight-chain $R_1$ preferably consist of 2-4 carbon atoms and branched-chain $R_1$ preferably of 3-5 carbon atoms. The hydroxy in $R_1$ can be primary and/or secondary hydroxy groups, but is present at a position other than the α-position of the hydroxyalkyl. Vicinal and geminal hydroxyl are therefore contemplated. $R_1$ can contain 1-5 hydroxy, but 1-3 hydroxy are preferred. Therefore, compounds of Formula I can contain a total of 4–20 hydroxy, preferably of 4–12 hydroxy.

Examples of $R_1$ include, but are not limited to, 2-hydroxyethyl, 2-hydroxypropyl, 3-hydroxypropyl, 2-hydroxy-1-methylpropyl, 3-hydroxy-1-methylpropyl, 1-(hydroxymethyl)-ethyl, 2-hydroxybutyl, 3-hydroxybutyl, 4-hydroxybutyl, 2-hydroxy-1-methylbutyl, 3-hydroxy-1-methylbutyl, 4-hydroxy-1-methylbutyl, 3-hydroxy-2-methylbutyl, 4-hydroxy-2-methylbutyl, 1,3-dihydroxyisopropyl, 3-hydroxyisobutyl, 2-hydroxy-1,1-dimethylethyl, 3-hydroxy-1,1-dimethylpropyl, 2,3-dihydroxypropyl, 2,3-dihydroxybutyl, 2,4-dihydroxybutyl, 3,4-dihydroxybutyl, 3-hydroxy-2-(hydroxymethyl)-propyl, 2,3-dihydroxy-1-methylpropyl, 2-hydroxy-3-(hydroxymethyl)-butyl, 2,3,4-trihydroxybutyl, 2,4-dihydroxy-3-(hydroxymethyl)-butyl, 2-hydroxy-2,2-bis(hydroxymethyl)propyl, 4-hydroxy-3,3-bis(hydroxymethyl)-butyl, 4-hydroxy-2,2-bis(hydroxymethyl)butyl and 2-hydroxy-1,1-bis(hydroxymethyl)ethyl.

Especially preferred $R_1$ are straight-chain or branched-chain of 2–3 carbon atoms substituted by one or two hydroxy, for example, 2-hydroxyethyl, 2-hydroxypropyl, 3-hydroxypropyl, 1-(hydroxymethyl)-ethyl, and 2,3-dihydroxypropyl.

Lower alkyl $R_2$ and $R_3$ and/or the branching groups on the alkylene in X are straight-chain alkyl of 1–4 carbon atoms, preferably 1–2 carbon atoms, for example, butyl, propyl, ethyl, and, preferably, methyl.

X is straight-chain or branched-chain alkylene, of 1–6 carbon atoms, which can be interrupted by one or more oxygen atoms. Straight-chain alkylene of 1–6 carbon atoms, interrupted by one or more, preferably by 1–4 oxygen atoms, is preferred. Expecially preferred is straight-chain alkylene of 1–4 carbon atoms, which can be interrupted by one to two oxygen atoms. In the oxaalkylene, the oxygen atoms will be separated from each other and from the ends thereof by at least one methylene.

Exemplary alkylene and oxaalkylene are: —$CH_2$—, —$(CH_2)_2$—, —$(CH_2)_4$—, —$CH_2$—O—$CH_2$—, —($CH_2$—$CH_2$—O—$CH_2$—$CH_2$)—, —$(CH_2$—O—$CH_2)_2$— and —$(CH_2$—O—$CH_2)_3$—.

Exemplary branched-chain X are: —[$C(CH_3)_2$]—, —[$CH_2$—$C(CH_3)_2$—$CH_2$]—, —[$CH_2$—$CH(CH_3)$—$CH(CH_3)$—$CH_2$]— and —[$CH_2$—$CH(CH_3)$—$CH_2$]—.

Compounds of Formula I therefore include those wherein:

(a) $R_1$ is alkyl of 2–8 carbon atoms, substituted by 1–5 hydroxy;

(b) $R_1$ is straight-chain alkyl of 2–4 carbon atoms or branched-chain alkyl of 3–5 carbon atoms, substituted by 1–3 hydroxy;

(c) $R_2$ is hydrogen, including each of (a)–(b);

(d) $R_2$ is alkyl of 1–4 carbon atoms, including each of (a)–(b);

(e) $R_2$ is $R_1$, including each of (a)–(b);

(f) $R_3$ is hydrogen, including each of (a)–(e);

(g) $R_3$ is alkyl of 1–4 carbon atoms, including each of (a)–(e);

(h) X is a direct bond, including each of (a)–(g);

(i) X is straight or branched chain alkylene of 1–6 carbon atoms, including each of (a)–(g); and (j) X is oxaalkylene, dioxaalkylene or trioxaalkylene of up to 6 carbon atoms, including each of (a)–(g).

Compounds of Formula II include each of (f)–(j), above.

Compounds of Formula I can be prepared by conventionally reacting a tetracarboxylic acid tetrachloride of Formula II

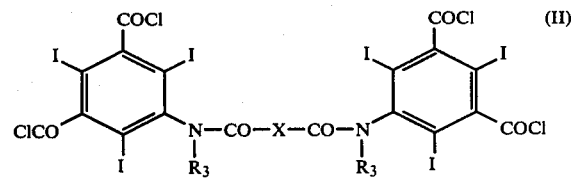

wherein $R_3$ and X are as above, with an amine

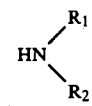

wherein $R_1$ and $R_2$ are as above.

The amidation reaction is preferably conducted in a polar solvent at 0°–100° C., more preferably at 15°–75° C., and most preferably at room temperature. Suitable solvents for the reaction are water, dioxane, tetrahydrofuran, methylene chloride, trichloroethylene, dimethylformamide, dimethylacetamide, and others, or mixtures thereof. Preferred solvents are water, dioxane, DMF, THF, DMA, and mixtures thereof.

The amine is preferably utilized in an excess. Any hydrogen chloride formed is bound by a corresponding molar excess of the amine. Most preferably, hydrogen chloride produced by the reaction is neutralized with a tetriary amine, for example, triethylamine, tributylamine, or pyridine, or with an alkali or alkaline earth hydroxide or carbonate, for example, KOH, NaOH, $Na_2CO_3$ and $Mg(OH)_2$.

Removal of inorganic salts formed by neutralization of liberated hydrogen chloride can be accomplished by the phenol extraction method described in DOS (German Unexamined Laid-Open Application) No. 2,031,724. Basic hydrochlorides thus formed can be removed from the reaction mixture with ion exchange columns customary in preparative organic chemistry.

Tetracarboxylic acid tetrachlorides of Formula II can be prepared by conventionally reacting a 2-4,6-triiodoisophthalic acid dichloride of Formula III

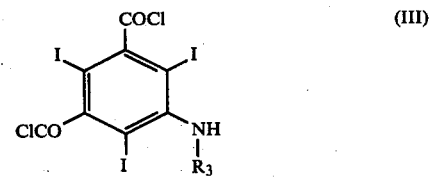

wherein $R_3$ is as above, with a dicarboxylic acid chloride of Formula IV

Compounds of Formula II are obtained from conventional 5-amino- or 5-alkylamino-2,4,6-triiodoisophthalic acid dichlorides by condensation with the dichloride of an aliphatic dicarboxylic acid of the formula Cl—CO—X—CO—Cl, wherein X is as above.

Suitable reaction media are organic solvents, e.g., aromatic hydrocarbons, such as chlorobenzene and toluene. Inert polar solvents, such as dimethylacetamide, N-methylpyrrolidone, dioxane and tetrahydrofuran, are preferred. Especially preferred solvents are, for example, dimethylacetamide, dioxane and tetrahydrofuran.

Dimeric tetracarboxylic acid tetrachlorides of Formula II formed during the reaction are either crystallized or isolated by concentration of the solutions under vacuum.

Surprisingly, even highly concentrated solutions of compounds of Formula I do not exceed the osmotic pressure of the blood. The novel compounds are distinguished from other compounds by a lower diffusibility on account of their size. As shown in Table I, using compounds E–H as examples, the osmotic pressure of compounds of Formula I is significantly lower than that of several important commercial preparations containing compounds of varying structures.

phy, lymphography, and for the visualization of various body cavities and for other radiological examinations.

Owing to their weak or neutral flavor, several of the compounds, even if not water-soluble, are very suitable for oral administration and for introduction into the lungs. The bitter and nauseating flavor of customary contrast media is a grave disadvantage, especially in gastrography and bronchography.

The novel compounds moreover have low toxicity as demonstrated by Table II, in which compounds E, F, G and I are compared with conventional commercial preparations meglumine amidotrizoate, meglumine iothalamate, meglumine iocarmate, and metrizamide, respectively.

1. Compatibility After Intravenous Injection

Each of 6–10 mice weighing 20–22 g. was injected intravenously with the contrast medium being tested in the form of a solution at a concentration of 300 mg. of iodine/ml., a dosage of 10 g. iodine/kg. and an injection rate of 0.8 ml./min. Ionic agents were given as meglu-

TABLE I

Concentration, Osmotic Pressure, and Osmolality of Solutions of Identical Iodine Concentration (300 mg. Iodine/ml.) for Compounds of Various Structural Types

| | | Structural Type | Concentration (mmol/l. Solution) | Osmotic Pressure (at.) at 37° C. | Osmolality (mOsm/kg . H$_2$O) at 37° C. |
|---|---|---|---|---|---|
| A. | Megluminamido-trizoate | Ionic, Monomeric | 1575 | 38.6 | 1520 |
| B. | Meglumine Iothalamate | Ionic, Monomeric | 1575 | 41.9 | 1650 |
| C. | Meglumine Iocarmate | Ionic, Dimeric | 1182 | 32.0 | 1260 |
| D. | Metrizamide | Nonionic, Monomeric | 788 | 12.3 | 485 |
| E. | Example 1 | Nonionic, Dimeric | 394 | 4.5 | 175 |
| F. | Example 8 | Nonionic, Dimeric | 394 | 5.7 | 224 |
| G. | Example 12 | Nonionic, Dimeric | 394 | 5.5 | 216 |
| H. | Example 9 | Nonionic, Dimeric | 394 | 5.0 | 197 |
| | Serum | — | — | 7.5 | 290 |

Compounds of Formula I accordingly are highly suitable as radiopaque agents for the preparation of and/or for use in x-ray contrast media. The novel compounds possess all properties required of x-ray contrast media. Many of these compounds, although nonionic, are very highly water-soluble. The novel compounds are highly compatible x-ray contrast media which are suitable for use in angiography, urography, myelogramine salts. All animals died after injection of the ionic contrast media and one animal died after injection of metrizamide. All mice survived following administration of the novel compound E.

TABLE II

| | Compound | Test | Compatibility After i.v. Injection in Mice LD$_{50}$ g. Iodine/kg. | Protein Binding Human Plasma n = 6 1.2 mg. Iodine/ml. | Effect of the Contrast Media on Erythrocyte Morphology 43 mg. Iodine/ml. Blood Damage Index |
|---|---|---|---|---|---|
| A. | Meglumine Amidotrizoate | | 6.5 | 3.2 ± 1.2 | 2.57 |
| B. | Meglumine Iothalamate | | 6.5 | 5.2 ± 0.3 | 2.34 |
| C. | Meglumine Iocarmate | | 6.5 | 9.2 ± 3.3 | 1.37 |
| D. | Metrizamide | | 14 | 6.2 ± 1.4 | 3.86 |
| E. | Example 1 | | 20 | 1.4 ± 2.4 | 0.33 |
| F. | Example 8 | | 10 | | 0.09 |
| G. | Example 12 | | 22 | | 0.13 |
| I. | Example 10 | | 30* | | 0.11 |

*Determined with supersaturated solution.

2. Protein Binding

Binding of contrast media to proteins of human plasma was determined at a final plasma concentration of 1.2 mg. iodine/ml. using the ultrafiltration method.

The novel, nonionic dimer E was bound only to a very minor extent of 1.4±2.4%. The comparison compounds all showed a higher protein affinity.

Binding to proteins is undesirable for contrast media used for angiography, urography, and myelography. Minor protein binding, as found for the novel dimer E, is considered an indication of good compatibility in accordance with Peter Knoefel, "Binding of Iodinated Radiocontrast Agents to the Plasma Proteins," in International Encyclopeida of Pharmacology and Therapeutics, Radiocontrast Agents, Vol. 1, (1971) Pergamon Press.

3. Effect on Erythrocytes

Contrast medium solutions containing 300 mg. iodine/ml. were mixed in a ratio of 1:6 with heparinized blood. The final concentration of the contrast media was 43 mg. iodine/ml. The evaluation criterion was the change of the natural shape of the erythrocytes via echinocytes to spherocytes. The score for intact erythrocytes was "0" and for the highest degree of damage was "5." Novel, nonionic dimers E-I caused substantially less damage to erythrocytes than conventional compounds. This finding is significant in two respects:

(a) A requirement for contrast media which are to be administered rapidly and in high doses is that they have a minimum influence on blood components.

(b) The extraordinarily minor damaging effect of the novel contrast medium on erythrocytes leads to the conclusion that the materials generally have low membrane-damaging effects.

Table II shows that compounds of Formula I are clearly superior to the conventional compounds A–D, especially with respect to protein binding and effect on erythrocytes.

In a further evaluation according to Valzelli, "A Simple Method to Inject Drugs Intracerebrally;" Med. Exp. Vol. 11: 23–26, (1964), each of 10 rats (90–110 g.) were injected intracerebrally with contrast medium solutions of compounds A-E at an iodine concentration of 50 mg./ml. in a dosage of 0.4 ml./kg. Toxic effects of compounds A–D included grave anomalies in posture (attitude), torsional spasms, excitation, and death. Novel compound E caused none of these effects in any of the animals and therefore has good neural compatibility.

The preparation of novel x-ray contrast media from compounds of Formula I is done by bringing the radiopaque compound, together with the additives customary in galenic pharmacy, into a form suitable for intravenous administration. Due to the low osmotic pressure of the novel compounds, it is possible for the very first time to add to the medium materials naturally occurring in the serum, particularly $Na^+$, $K^+$, $Ca^{++}$, $Mg^{++}$, $CO_3^{2-}$, $PO_4^{3-}$, $SO_4^{2-}$, $Cl^-$, glucose, and amino acids, as well as substances employed in galenic pharmacy, namely meglumine EDTA, or substances for adjustment of colloid-osmotic pressure, as utilized in liquid blood substitutes, e.g., dextrans, poly-N-vinylpyrrolidone, without placing an additional osmotic load on the organism receiving the medium.

The compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, viscous paraffin, perfume oil, fatty acid monoglycerides and diglycerides, pentaerythritol fatty acid esters, hydroxy methylcellulose, polyvinyl pyrrolidone, talc, etc.

For parenteral application, particularly suitable are solutions, preferably oily or aqueous solutions, as well as suspensions or emulsions. Ampoules are convenient unit dosages.

For enteral application, particularly suitable are tablets or dragees having talc and/or a carbohydrate carrier or binder or the like, the carrier preferably being lactose and/or corn starch and/or potato starch. A syrup or the like can be used wherein a sweetened vehicle is employed. Sustained release compositions can also be formulated wherein the active compound is protected with differentially degradable coatings, e.g., by microencapsulation, multiple coatings, etc.

For intravenous administration the compounds of this invention are preferably used in aqueous solution whereby the concentration of active compound is between about 15% by volume and about 75% by volume. Generally the amount of active agent per unit dosage is about 5 to 50 g., preferably 7 to 35 g.

The solutions have a relative low viscosity and can be administered by intravenous injection and are furthermore distinguished by good circulatory compatibility and low toxicity.

The concentration of novel x-ray contrast media in an aqueous medium is entirely dependent on the roentgenographic method of diagnosis. Preferred concentrations and dosages of the novel compounds are concentrations of 30–450 mg. I/ml. and dosages of 3–250 ml. Concentrations between 250 and 400 mg. I/ml. are particularly preferred.

Compounds which do not have a strong flavor are e.g.

Oxalic Acid bis[3,5-bis(2-Hydroxyethylcarbamoyl)-2,4,6-triiodoanilide]

Oxalic Acid bis[3,5-bis(N,N-bis{2-Hydroxyethyl}-carbamoyl)-2,4,6-triiodoanilide]

Oxalic Acid bis[3,5-bis(3-Hydroxypropylcarbamoyl)-2,4,6-triiodoanilide]

Oxaglutaric Acid bis[3,5-bis(2,4-Dihydroxypropyl-N-methylcarbamoyl)-2,4,6-triiodo-N-methylanilide]

Adipic Acid bis[3,5-bis(1,3-Dihydroxyisopropylcarbamoyl)-2,4,6-triiodoanilide]

The following examples serve to further explain the present invention.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

Oxalic Acid bis[3,5-bis(2,3-Dihydroxypropyl-N-methylcarbamoyl)-2,4,6-triiodoanilide)

(a) A solution of 103 g. of 5-aminotriiodoisophthalic acid dichloride in 412 ml. of dioxane is stirred and heated in an oil bath at 80°–90° C. internal temperature and combined within 10 minutes dropwise with 10.3 ml. of oxalic acid dichloride. After 2 hours of agitation and heating, the novel compound is crystallized; this can be accelerated by inoculation. After agitation overnight at room temperature, the sediment is vacuum-filtered and dried with the exclusion of moisture.

Yield of crude oxalic acid di-(3,5-dichlorocarbonyl-2,4,6-triiodoanilide): 88.5 g. = 73.6% of theory, taking into account a dioxane content of 10% by weight. Melting point: no decomposition up to 320° C.

(b) A solution of 88.5 g. of the above tetra-acid tetrachloride in 1.77 l. of dioxane is combined at room temperature with thorough agitation with 90 g. of N-methylamino-2,3-propanediol and 177 ml. of water and stirred at room temperature for 48 hours. The emulsion is then dried. The oily residue is combined under agitation with three 900 ml. portions of isopropanol, vacuum-filtered, and dried. Thereafter, the residue is dissolved in 1 l. of water and passed over a column of a cation exchanger. From the first fractions, 102 g. of an oil is isolated which, dissolved in 1 l. of water, is passed over an anion exchanger. From the first fractions, after treatment with carbon and concentration, 56 g. = 58% of theory of oxalic acid bis[3,5-bis(2,3-dihydroxypropyl-N-methylcarbamoyl)-2,4,6-triiodoanilide] is obtained. Melting point with decomposition: 307°–312° C.

| Analysis: | Calculated | Found |
|---|---|---|
| Iodine | 50.1% | 50.2% |
| N | 5.5% | 5.7% |

Solubility in water > 60 g./100 ml. of solution at room temperature.

EXAMPLE 2

Oxalic Acid bis[3,5-bis(2-Hydroxyethylcarbamoyl)-2,4,6-triiodoanilide]

A suspension of 28 g. of crude oxalic acid di-(3,5-dichlorocarbonyl-2,4,6-triiodoanilide) of 10% dioxane content (prepared according to Example 1a) in 400 ml. of dioxane is combined dropwise under agitation with a solution of 6.1 g. of ethanolamine in 50 ml. of water and simultaneously with a solution of 10 g. of potassium bicarbonate in 50 ml. of water. After agitating the reaction mixture overnight, the suspension is concentrated to dryness under vacuum, and the thus-produced oil is triturated with heating with 100 ml. of ethanol. The product is crystallized with cooling. The product is extracted with 130 ml. of water, vacuum-filtered, and dried.

Yield of oxalic acid bis[3,5-bis(2-hydroxyethylcarbamoyl)-2,4,6-triiodoanilide]: 20.4 g. = 76% of theory.

| Analysis: | Calculated | Found |
|---|---|---|
| Iodine | 56.66% | 56.40% |
| N | 6.25% | 6.41% |

No decomposition up to 320° C.

EXAMPLE 3

Oxalic Acid bis[3,5-bis(2-Hydroxyethyl-N-methylcarbamoyl)-2,4,6-triiodoanilide]

A solution of 12.45 g. (calculated without dioxane) of oxalic acid di-(3,5-dichlorocarbonyl-2,4,6-triiodoanilide) in 160 ml. of dioxane is combined with 10 g. of N-methylethanolamine. After agitation overnight, the dioxane is poured off. The oily residue is combined with 140 ml. of water and adjusted to pH 1 with hydrochloric acid. After stirring overnight, the precipitate is vacuum-filtered.

Yield: 7.4 g. = 52.9% of theory of the title compound. Decomposition starting at 290° C.

EXAMPLE 4

Oxalic Acid bis[3,5-bis(N,N-bis{2-Hydroxyethyl}-carbamoyl)-2,4,6-triiodoanilide]

Analogously to Example 3, this compound is obtained from 10 millimoles of oxalic acid di-(3,5-dichlorocarbonyl-2,4,6-triiodoanilide) and 120 millimoles of diethanolamine. The reaction product is worked up as set forth in Example 3.

EXAMPLE 5

Oxalic Acid bis[3,5-bis(2-Hydroxyethylcarbamoyl)-2,4,6-triiodoanilide]

A suspension of 24.9 g. (calculated without dioxane) of oxalic acid di-(3,5-dichlorocarbonyl-2,4,6-triiodoanilide) in 125 ml. of dimethylformamide is combined with 15 g. of ethanolamine. After an exothermic reaction to 55° C., a solution is thus obtained. After agitation for several hours, the solvent is distilled off under vacuum. The oily residue is combined with 250 ml. of water and acidified to pH 1 with hydrochloric acid. The precipitate is vacuum-filtered and extracted with water.

Yield: 26.4 g. = 98.2% of theory of oxalic acid bis[3,5-bis(2-hydroxyethylcarbamoyl)-2,4,6-triiodoanilide]. No decomposition up to 320° C.

EXAMPLE 6

Oxalic Acid bis[3,5-bis(3-Hydroxypropylcarbamoyl)-2,4,6-triiodoanilide]

This compound is obtained analogously to Example 5 from 10 millimoles of oxalic acid di-(3,5-dichlorocarbonyl-2,4,6-triiodoanilide) and 120 millimoles of 3-amino-1-propanol.

EXAMPLE 7

Oxalic Acid bis[3,5-bis(2-Hydroxypropylcarbamoyl)-2,4,6-triiodoanilide]

This compound is prepared analogously to Example 5 from 10 millimoles of oxalic acid di-(3,5-dichlorocarbonyl-2,4,6-triiodoanilide) and 120 millimoles of 1-amino-2-propanol.

EXAMPLE 8

Oxaglutaric Acid bis[3,5-bis(2,3-Dihydroxypropyl-N-methylcarbamoyl)-2,4,6-triiodo-N-methylanilide]

(a) A solution of 110 g. of 5-methylamino-2,4,6-triiodoisophthalic acid dichloride in 110 ml. of dioxane is combined dropwise with agitation at 80° C. with 18.5 g. of 2-oxaglutaric acid dichloride. Thereafter, the reaction mixture is refluxed for 5.5 hours, thus producing a precipitate. The latter is vacuum-filtered after 20 hours of agitation.

Yield: 60.5 g.=51% of theory of oxaglutaric acid bis(3,5-bis-chlorocarbonyl-2,4,6-triiodo-N-methylanilide). Decomposition at about 300° C., dioxane content°0.5%.

| Analysis: | Calculated | Found |
|---|---|---|
| Cl | 10.76% | 11.3% |
| I | 57.79% | 57.7% |

(b) Under vigorous agitation, a solution of 31.5 g. of N-methylamino-2,3-propanediol in 60 ml. of tetrahydrofuran is added dropwise to a solution of 39.7 g. of the above tetracarboxylic acid tetrachloride in 317 ml. of tetrahydrofuran. An oily precipitate is thus obtained, from which the tetrahydrofuran is decanted after agitation overnight. The precipitate is dissolved in 400 ml. of water and passed over a column with 500 g. of cation exchanger, e.g., IR 120. The eluates, concentrated to 400 ml., are passed over 500 g. of anion exchanger, e.g., IRA 410. The combined eluates are concentrated, treated with carbon, and dried.

Yield: 37.7 g.=78% of theory of oxaglutaric acid bis[3,5-bis(2,3-dihydroxypropyl-N-methylcarbamoyl)-2,4,6-triiodo-N-methylanilide].

| Decomposition starting at 222° C. | | |
|---|---|---|
| Analysis: | Calculated | Found |
| I | 47.82 % | 47.5 % |

Solubility in water more than 60 g./100 ml. of solution.

EXAMPLE 9

Malonic Acid bis[3,5-bis(2,3-Dihydroxypropyl-N-methylcarbamoyl)-2,4,6-triiodo-N-methylanilide]

(a) A solution of 30.5 g. of 5-methylamino-2,4,6-triiodoisophthalic acid Dichloride in 45 ml. of dioxane is gradually combined under reflux with 4.2 g. of malonyl chloride and heated for 3 hours more. After cooling, the precipitate is vacuum-filtered.

Yield: 25.8 g.=80% of theory of malonic acid bis(3,5-bis-chlorocarbonyl-2,4,6-triiodo-N-methylanilide).

Dioxane content: 0.8%. Melting point above 300° C.

(b) A suspension of 20 g. of the above tetracarboxylic acid tetrachloride in 260 ml. of tetrahydrofuran is stirred together with a solution of 16.3 g. of N-methylaminopropanediol in 40 ml. of tetrahydrofuran for 24 hours. Thereafter, the oily crude product is isolated in pure form as in Example 8(b) by treatment with an ion exchanger.

Yield: 22 g.=91% of theory, melting point 233°-250° C., of malonic acid bis[3,5-bis(2,3-dihydroxypropyl-N-methylcarbamoyl)-2,4,6-triiodo-N-methylanilide].

Solubility in water: more than 60 g./150 ml. of solution.

EXAMPLE 10

Adipic Acid bis[3,5-bis(2,3-Dihydroxypropyl-N-methylcarbamoyl)-2,4,6-triiodoanilide]

(a) Under reflux, 41 g. of adipic acid dichloride is added dropwise to a solution of 221 g. of 5-aminotriiodoisophthalic acid dichloride in 320 ml. of dioxane. After heating the reaction mixture for 3 hours and then cooling same overnight, the precipitate is vacuum-filtered.

Yield: 169 g.=67% of theory of adipic acid bis(3,5-bis-chlorocarbonyl-2,4,6-triiodoanilide) with 6% dioxane. Decomposition starting with 292° C.

(b) Analogously to Example 8(b), a solution of 133 g. of the above-mentioned tetracarboxylic acid chloride in 1000 ml. of tetrahydrofuran is combined with a solution of 101 g. of N-methylaminopropanediol in 300 ml. of tetrahydrofuran and, after agitation overnight, purified by dissolving the oily crude product in water and chromatography over ion exchange columns.

Yield: 98.2 g.=64% of theory, melting point 233°-244° C., of adipic acid bis[3,5-bis(2,3-dihydroxypropyl-N-methylcarbamoyl)-2,4,6-triiodoanilide].

Solubility in water: 13%.

The compound yields supersaturated solutions.

EXAMPLE 11

Adipic Acid bis[3,5-bis(1,3-Dihydroxyisopropylcarbamoyl)-2,4,6-triiodoanilide]

A mixture of 27.6 g. of adipic acid bis(3,5-bis-chlorocarbonyl-2,4,6-triiodoanilide) and 18 g. of 1,3-dihydroxyisopropylamine in 260 ml. of tetrahydrofuran is vigorously agitated for 48 hours. The precipitate is then vacuum-filtered and washed with water.

Yield: 21.3 g.=70% of theory of adipic acid bis[3,5-bis(1,3-dihydroxyisopropylcarbamoyl)-2,4,6-triiodoanilide].

Decomposition above 300° C.; solubility in water: below 0.1%.

EXAMPLE 12

3,6-Dioxasuberic Acid bis[3,5-bis(2,3-Dihydroxypropyl-N-methylcarbamoyl)-2,4,6-triiodoanilide]

(a) Under reflux, 25.8 g. of dioxasuberic acid dichloride is added dropwise to a solution of 119 g. of 5-aminotriiodoisophthalic acid dichloride in 119 ml. of dioxane. After heating the reaction mixture for 6 hours and cooling overnight, the precipitate is vacuum-filtered. Yield: 75 g.=52% of theory of 3,6-dioxasuberic acid bis(3,5-bis-chlorocarbonyl-2,4,6-triiodoanilide) with 6.8% dioxane; decomposition 260°-262° C.

(b) A solution of 71 g. of the above-mentioned tetracarboxylic acid chloride and 35 g. of tributylamine in 375 ml. of dimethylacetamide is heated to 50° C. and then combined dropwise with a solution of 26 g. of N-methylaminopropanediol in 200 ml. of dimethylacetamide. After another 4 hours of agitation and cooling overnight, the solvent is distilled off under vacuum, and the residue is stirred with methylene chloride. The product insoluble in the methylene chloride is dissolved in 750 ml. of water and purified on ion exchange columns analogously to Example 8(b).

Yield: 45 g.=56% of theory of 3,6-dioxasuberic acid bis[3,5-bis(2,3-dihydroxypropyl-N-methylcarbamoyl)-2,4,6-triiodoanilide]. Melting point: 214°-220° C. (decomposition).

EXAMPLE 13

Preparation of a Blood-Isotonic Solution with the Compound of Example 8:

Oxaglutaric acid bis[3,5-bis(2,3-

-continued

| | |
|---|---|
| dihydroxypropyl-N-methylcarbamoyl)-2,4,6-triiodo-N-methylanilide] | 62.74 g. |
| NaCl | 0.24 g. |
| Ca,Na$_2$ Edetate | 0.01 g. |
| 1N NaOH to adjust to pH 7 | |
| Twice distilled water | to 150 ml. |

The solution is charged into bottles or ampoules and sterilized.

Iodine content: 300 mg./ml.

Osmolality at 37° C. 290 m Osm. corresponding to 7.5 at.

EXAMPLE 14

Preparation of a Blood-Isotonic Solution, the Cation Content of Which is Adapted to That of Human Serum:

| | |
|---|---|
| Oxalic acid bis[3,5-bis(2,3-dihydroxypropyl-N-methylcarbamoyl)-2,4,6-triiodo-anilide] | 59.890 g. |
| CaCl$_2$ . 2H$_2$O | 0.022 g. |
| KCl | 0.032 g. |
| MgCl$_2$ . 6H$_2$O | 0.017 g. |
| NaHCO$_3$ | 0.050 g. |
| NaCl | 0.170 g. |
| Na$_2$ Edetate | 0.010 g. |
| 1N NaOH to adjust to pH 7 | |

The solution is bottled under aseptic conditions or subsequently sterilized.

Iodine content: 300 mg./ml.

Osmolality at 37° C. 290 m. Osm. corresponding to 7.5 at.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

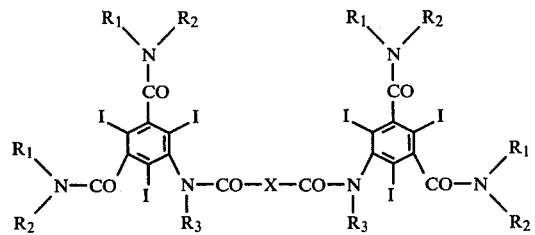

wherein $R_1$ is alkyl of 2–8 carbon atoms substituted by 1–5 hydroxyl on separate carbon atoms thereof, other than the α-carbon atom;

$R_2$ is hydrogen, alkyl of up to 4 carbon atoms or $R_1$;

$R_3$ is hydrogen or alkyl of 1–4 carbon atoms;

X is a direct bond or straight-chain or branched-chain alkylene, oxaalkylene, dioxaalkylene, or trioxaalkylene of up to 6 carbon atoms, wherein the oxygen atoms of the di- and trioxaalkylenes are separated from each other and from the ends thereof by at least one methylene.

2. Oxalic acid bis[3,5-bis(2,3-dihydroxypropyl-N-methylcarbamoyl)-2,4,6-triiodoanilide], a compound of claim 1.

3. Oxalic acid bis[3,5-bis(2-hydroxyethylcarbamoyl)-2,4,6-triiodoanilide], a compound of claim 1.

4. Oxalic acid bis[3,5-bis(2-hydroxyethyl-N-methylcarbamoyl)-2,4,6-triiodoanilide], a compound of claim 1.

5. Oxalic acid bis[3,5-bis(N,N-bis[2-hydroxyethyl]-carbamoyl)-2,4,6-triiodoanilide], a compound of claim 1.

6. Oxalic acid bis[3,5-bis(3-hydroxypropylcarbamoyl)-2,4,6-triiodoanilide], a compound of claim 1.

7. Oxalic acid bis[3,5-bis(2-hydroxypropylcarbamoyl)-2,4,6-triiodoanilide], a compound of claim 1.

8. Oxaglutaric acid bis[3,5-bis(2,3-dihydroxypropyl-N-methylcarbamoyl)-2,4,6-triiodo-N-methylanilide], a compound of claim 1.

9. Malonic acid bis[3,5-bis(2,3-dihydroxypropyl-N-methylcarbamoyl)-2,4,6-triiodo-N-methylanilide], a compound of claim 1.

10. Adipic acid bis[3,5-bis(2,3-dihydroxypropyl-N-methylcarbamoyl)-2,4,6-triiodoanilide], a compound of claim 1.

11. Adipic acid bis[3,5-bis(1,3-dihydroxyisopropylcarbamoyl)-2,4,6-triiodoanilide], a compound of claim 1.

12. 3,6-Dioxasuberic acid bis[3,5-bis(2,3-dihydroxypropyl-N-methylcarbamoyl)-2,4,6-triiodoanilide], a compound of claim 1.

13. A compound of the formula

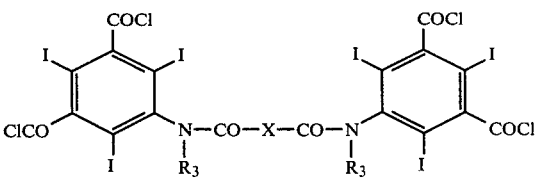

wherein $R_3$ is H or alkyl and X is a direct bond or straight-chain or branched-chain alkylene oxaalkylene, dioxaalkylene, or trioxaalkylene of up to 6 carbon atoms, wherein the oxygen atoms on the di- and trioxaalkylenes are separated from each other and from the ends thereof by at least one methylene.

14. Oxalic acid bis[3,5-bis(chlorocarbonyl)-2,4,6-triiodoanilide], a compound of claim 13.

15. Oxaglutaric acid bis[3,5-bis(chlorocarbonyl)-2,4,6-triiodo-N-methylanilide], a compound of claim 13.

16. Malonic acid bis[3,5-bis(chlorocarbonyl)-2,4,6-triiodo-N-methylanilide], a compound of claim 13.

17. Adipic acid bis[3,5-bis(chlorocarbonyl)-2,4,6-triiodoanilide], a compound of claim 13.

18. 3,6-Dioxasuberic acid bis[3,5-bis(chlorocarbonyl)-2,4,6-triiodoanilide], a compound of claim 13.

19. An x-ray contrast agent adapted for oral or intravenous administration comprising a radiopaque amount per unit dosage of a compound of claim 1, in admixture with a pharmaceutically acceptable carrier.

20. A method for conducting a radiological examination of a patient which comprises administering thereto prior to examination a radiopaque amount of a compound of claim 1.

* * * * *

UNITED STATES PATENT AND TRADEMARK OFFICE

CERTIFICATE EXTENDING PATENT TERM
UNDER 35 U.S.C. 156

Patent No.    : 4,239,747

Dated         : December 16, 1980

Inventor(s)   : Heinrich Pfeiffer et al

Patent Owner  : Schering Aktiengesellschaft

This is to certify that there has been presented to the

COMMISSIONER OF PATENTS AND TRADEMARKS an application under 35 U.S.C. 156 for an extension of the patent term. Since it appears that the requirements of the law have been met, this certificate extends the term of the patent for the period of

2 YEARS with all rights pertaining thereto as provided by 35 USC 156 (b).

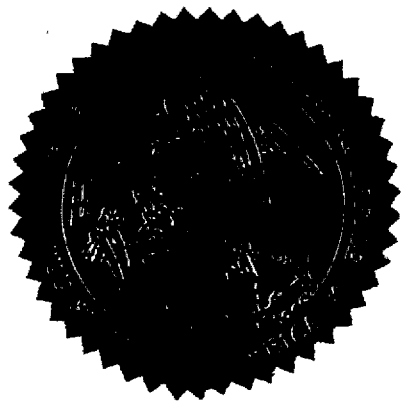

I have caused the seal of the Patent and Trademark Office to be affixed this 7th day of December 1990.

Harry F. Manbeck, Jr.
Assistant Secretary and Commissioner of Patents and Trademarks